United States Patent [19]

Bittler et al.

[11] Patent Number: 4,542,128
[45] Date of Patent: Sep. 17, 1985

[54] 17α-PREGN-4-ENE-3-OXO-21-CARBOXYLIC ACID ESTERS, PROCESS FOR THE PREPARATION THEREOF, AND USE THEREOF AS MEDICINAL AGENTS

[75] Inventors: Dieter Bittler; Henry Laurent; Klaus Nickisch; Rudolf Weichert, all of Berlin; Jorge Casals-Stenzel, Mainz, all of Fed. Rep. of Germany

[73] Assignee: Schering Aktiengesellschaft, Berlin & Bergkamen, Fed. Rep. of Germany

[21] Appl. No.: 516,398

[22] Filed: Jul. 22, 1983

[30] Foreign Application Priority Data

Jul. 22, 1982 [DE] Fed. Rep. of Germany ....... 3227597

[51] Int. Cl.[4] .............................................. A61K 31/33
[52] U.S. Cl. .................................. 514/177; 260/397.1; 260/239.57
[58] Field of Search .................... 424/240; 260/239.57, 260/397.1

[56] References Cited

U.S. PATENT DOCUMENTS 3,919,199 11/1975 Lenz ................... 260/239.57
4,180,570 12/1979 Wiechert et al. ............. 260/239.57
4,291,029 9/1981 Wiechert et al. ............. 260/239.57

OTHER PUBLICATIONS

Chinn & al., J. Org. Chem., vol. 40, No. 9, 1975, pp. 1328–1331.

Primary Examiner—Elbert L. Roberts
Attorney, Agent, or Firm—Millen & White

[57] ABSTRACT

17α-Pregn-4-ene-3-oxo-21-carboxylic acid esters of Formula I

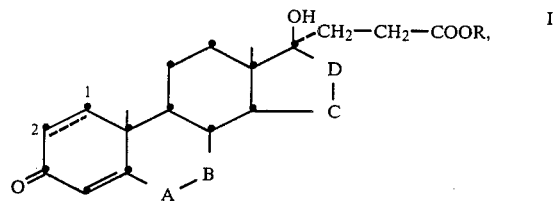

wherein $C_1 \text{---} C_2$ is a CC single or C=C double bond, —A—B— is

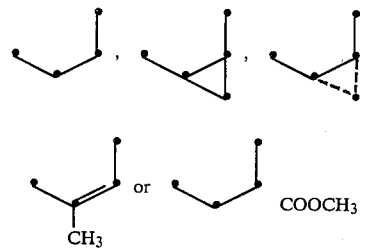

—C—D— is

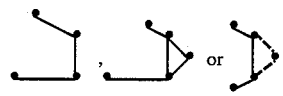

and R is an alkyl or alkenyl residue of up to 6 carbon atoms, in addition to antialdosterone activity, exhibit greatly reduced antiandrogenic and progestational side effects.

21 Claims, No Drawings

17α-PREGN-4-ENE-3-OXO-21-CARBOXYLIC ACID ESTERS, PROCESS FOR THE PREPARATION THEREOF, AND USE THEREOF AS MEDICINAL AGENTS

BACKGROUND OF THE INVENTION

The present invention relates to new steroidal compounds which have valuable pharmacological properties.

For the treatment of certain forms of hypertonia, of edemas, of primary aldosteronism, and of other endocrinological imbalances caused by aldosterone, and for use as diuretics, compounds are utilized which reverse the effect of aldosterone or deoxycorticosterone on the excretion of sodium and potassium salts. These include as their most well-known representative the compound spironolactone, which has been available commercially for some time. However, frequently, undesirable endocrinic side effects occur in the treatment with spironolactone. These are evoked by the antiandrogenic and progestational activity of spironolactone. Thus, with a relatively long-term treatment of male patients with spironolactone, occurrence of gynecomastia is observed (Smith, W. G., The Lancet, 1962, p. 886; Mann, N. M., JAMA 1963, p. 778; Clark, E., JAMA 1965, p. 157; Greenblatt,t D. J., JAMA 1973, p. 82) and impotence is observed as well (Greenblatt, D. J., JAMA 1973, p. 82), due to the antiandrogenic side effect of this active agent (Steelman, S. L. et al., Steroids 1963, p. 449; Schane, H. P., J. of Clinical Endocrinology and Metabolism 1978, p. 691).

In contrast, the progestational side effect of spironolactone is blamed for secondary symptoms such as amenorrhea and cycle irregularities occurring in women when treated with spironolactone. Both side effects can be confirmed in animal experiments as well as in vitro by receptor binding tests with the androgen and progestogen receptor, respectively.

SUMMARY OF THE INVENTION

It is an object of the present invention to provide compounds which are not essentially equivalent or superior to spironolactone in antialdosterone effect, but exhibit greatly diminished antiandrogen and progestational side effects.

Upon further study of the specification and appended claims, further objects and advantages of this invention will become apparent to those skilled in the art.

These objects have been achieved by providing novel 17α-pregn-4-ene-3-oxo-21-carboxylic acid esters of Formula I

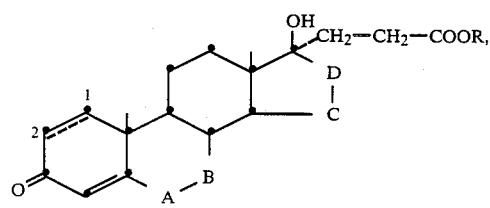

wherein
$C_1$------$C_2$ is a CC single or C=C double bond,
—A—B— is

—C—D— is

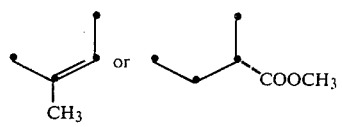

and
R is an alkyl or alkenyl residue of up to 6 (e.g., 2-6) carbon atoms.

DETAILED DISCUSSION

Examples of suitable alkyl residues R include methyl, ethyl, propyl, butyl, pentyl, hexyl, isobutyl, and tert-butyl, and of suitable alkenyl residues, vinyl, allyl, and methallyl.

The antialdosterone activity was determined and measured in a test model by Hollmann, G. Hollmann et al., "Tubulaere Wirkungen und renale Elimination von Spironolactonen" [Tubular Effects and Renal Elimination of Spironolactones], Naunyn-Schmiedebergs Arch. Exp. Path. Pharmak. 247: 419 [1964]; P. Marx, "Renale Wirkungen des d-Aldosterons und seines Antagonisten Spironolacton" [Renal Effects of d-Aldosterone and Its Antagonist Spironolactone], Diss. Med. Fak. FU Berlin, 1966, all of whose disclosures are incorporated by reference herein.

ANDROGEN RECEPTOR BINDING TEST

The androgen receptor (protein) contained in the cytosol of a homogenate of rate prostates binds dihydrotestosterone (DHT) with high affinity but low capacity. If this recptor is loaded with $^3$H-DHT in the presence of the compound to be tested, then the extent to which $^3$H-DHT is displaced from the receptor depends on the concentration and binding affinity of the compound to be tested. After separation of the receptor-bound DHT from the unbound DHT, the binding can be determined in percent, and this value is plotted against the logarithm of the molar concentration of the test compound. The concentration of the test compound is now determined which is required for entirely displacing the reference compound from the receptor. The competition factor (CF) as a measure for the binding strength is defined as the ratio of concentration of test compound to the concentration of reference compound, so that a high CF value indicates low binding strength, but a low CF value indicates high affinity.

The progestogen receptor binding test takes place in the same way with the use of cytosol from rat uterus homogenate.

Antiandrogenic activity is found in compounds which, although themselves lacking androgenic activity, due to their high binding affinity, displace the body's own androgen from the receptor entirely or partially. This is observed to a certain extent with spironolactone. For this reason, a high competition factor is desirable in the androgen and progestogen receptor test.

The following table compiles the relative values of antialdosterone efficacy (with spironolactone=1) and of the competition factors in the androgen receptor test ($C_A$) and in the progestogen receptor test ($C_G$) of spironolactone and of the compounds of this invention, using as indicative examples:

I  17-hydroxy-3-oxo-17α-pregn-4-ene-6β,7β; 15β,16β-dimethylene-21-carboxylic acid methyl ester, II  17-hydroxy-3-oxo-17α-pregna-1,4-diene-6β,7β; 15β,16β-dimethylene-21-carboxylic acid methyl ester, III  17-hydroxy-3-oxo-17α-pregn-4-ene-6β,7β; 15β,16β-dimethylene-21-carboxylic acid ethyl ester, IV  17-hydroxy-3-oxo-17α-pregn-4-ene-6β,7β;15β,16β-dimethylene-21-carboxylic acid propyl ester, V  17-hydroxy-3-oxo-17α-pregna-1,4-diene-6β,7β;15β,16β-dimethylene-21-carboxylic acid butyl ester, VI  17-hydroxy-3-oxo-17α-pregn-4-ene-6β,7β;15β,16β-dimethylene-21-carboxylic acid pentyl ester.

TABLE

| Compound | Relative Antialdosterone Activity | Competition Factor | |
|---|---|---|---|
| | | $C_A$ | $C_G$ |
| Spironolactone | 1 | 8.9 | 21 |
| I | ~0.6 | 33 | 25 |
| II | >1 | 18 | 41 |
| III | 1.5–2.0 | 27 | 19 |
| IV | >1 | 21 | 18 |
| V | ~1.0 | 14 | 57 |
| VI | >1.0 | 43 | 107 |

As the table shows, the compounds of this invention show an equivalence to or even a superiority over spironolactone with respect to their primary activity as antialdosterones, but, regarding the side effects, exhibit a surprisingly greatly reduced binding to the progestogen and androgen receptor, respectively.

Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oily or aqueous solutions, as well as suspensions, emulsions, or implants, including suppositories. Ampules are convenient unit dosages.

For enteral application, particularly suitable are tablets, dragees, suppositories or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Dosages for a given host for a given indication can be determined, e.g., by customary comparison of the activities of the subject compound and of a known agent by means of an appropriate, conventional pharmacological protocol, e.g., those described above.

Thus, this invention furthermore relates to medicinal agents having antialdosterone activity containing a compound of Formula I. These pharmacologically effective compounds of Formula I can be utilized by conventional methods of gelenic pharmacy for preparing medicines, especially those for oral administration. These compounds can be used in mammals including humans for the purposes for which spironolactone is used, e.g., for the purposes mentioned above.

The dosage of the compound of this invention or of a mixture of several of these compounds of Formula I is, in human patients, 20–500 mg/day in total amount of active agent for the above-mentioned treatments. Unit dosages will be provided accordingly, e.g., 10–100 mg. Administration will be analogous to that of the conventional agent, spironolactone.

This invention furthermore relates to a process for the preparation of 17α-pregn-4-ene-3-oxo-21-carboxylic acid esters of Formula I, comprising conventionally reacting a compound of Formula II

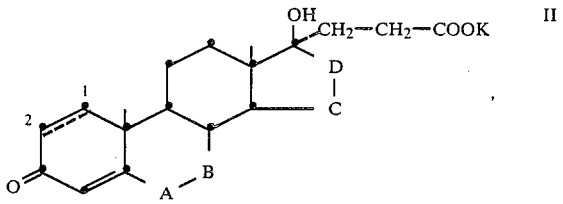

wherein $C_1\text{------}C_2$, —A—B—, and —C—D— are as defined for Formula I, with a compound R Hal wherein R is as defined for Formula I and Hal is chlorine, bromine, or iodine, in an aprotic solvent at temperatures of room temperature to 120° C.

All solvents or mixtures thereof which are inert with respect to the reactants can be utilized in the reaction. Suitable ones include aprotic, water-miscible solvents, such as dimethylformamide, dimethylacetamide, hexamethylphosphoric triamide, tetrahydrofuran, acetonitrile, dioxane, ethylene glycol dimethyl ether, diethylene glycol dimethyl ether, and triethylene glycol dimethyl ether.

The reaction, in conventional dependence on the version of the substituent R or Hal or on the selected reaction temperature, is completed after one hour or only after 3 days. Suitably, the reaction is carried out at room temperature. It is recommended to control the reaction by thin-layer chromatography. The reaction mixture is worked up once the starting material has been converted, as usual, for example by precipitation, extraction, recrystallization and/or column chromatography.

All of the starting materials are known and/or readily preparable using fully conventional methods starting with known compounds.

Starting carbolactones are described in U.S. Pat. No. 4,129,564 and U.S. application Ser. No. 361,164 of Mar. 23, 1982.

For instance, as shown in the following examples the potassium salts of formula II can be prepared from the corresponding known carbolactones by reaction with KOH in a lower alkanol (e.g., methanol, propanol, etc.) at a temperature of about 60° C. to reflux temperatures for a short time, e.g., about 30 minutes, followed by conventional work-up. The reaction of carbolactones with KOH is described in U.S. application Ser. No. 361,164 of Mar. 23, 1982.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(A) A solution of 10.0 g of 3-oxo-17α-pregn-4-ene-21,17-carbolactone in 30 ml of methanol is combined with a solution of 3.3 g of potassium hydroxide in 50 ml of methanol as well as 2 g of active carbon and heated to boiling for 30 minutes. The mixture is suctioned off in the hot state, washed with 20 ml of methanol, and the filtrate is stirred into 1000 ml of diethyl ether. The thus-precipitated 17-hydroxy-3-oxo-17α-pregn-4-ene-21-carboxylic acid potassium salt is suctioned off and dried under vacuum.

(B) 4.0 g of 17-hydroxy-3-oxo-17α-pregn-4-ene-21-carboxylic acid potassium salt is stirred with 4 ml of methyl iodide in 40 ml of dimethyl sulfoxide for one hour at room temperature. The reaction mixture is introduced into ice water which contains sodium chloride; the precipitated product is filtered off and taken up in dichloromethane. The solution is washed with sodium bicarbonate solution and water, dried, and evaporated under vacuum. The residue is chromatographed on silica gel. With 32–34% ethyl acetate-hexane, 1.51 g is eluted which is crystallized from diethyl ether-petroleum benzin, thus obtaining 1.27 g of 17-hydroxy-3-oxo-17α-pregn-4-ene-21-carboxylic acid methyl ester, mp 145° C. $[\alpha]_D = +62°$ (chloroform). UV: $\epsilon_{240} = 16,500$ (methanol).

EXAMPLE 2

Under the conditions set forth in Example 1(B), 4.0 g of 17-hydroxy-3-oxo-17α-pregn-4-ene-21-carboxylic acid potassium salt is reacted with 4 ml of ethyl bromide. The crude product is chromatographed on silica gel. With 20–30% ethyl acetate-hexane, 1.48 g of eluted which is crystallized from diethyl ether-petroleum benzine. Yield: 1.17 g of 17-hydroxy-3-oxo-17α-pregn-4-ene-21-carboxylic acid ethyl ester, mp 116° C. $[\alpha]_D = +55°$ (chloroform).

UV: $\epsilon_{240} = 16,100$ (methanol).

EXAMPLE 3

4.0 g of 17-hydroxy-3-oxo-17α-pregn-4-ene-21-carboxylic acid potassium salt is stirred with 3 ml of propyl bromide in 20 ml of dimethyl sulfoxide for 30 minutes at room temperature. Working up takes place as described in Example 1(B). The crude product is chromatographed on silica gel. With 36–43% ethyl acetate-hexane, 2.42 g of an oil is obtained. Crystallization from diethyl ether-diisopropyl ether yields 975 mg of 17-hydroxy-3-oxo-17α-pregn-4-ene-21-carboxylic acid propyl ester, mp 87° C. $[\alpha]_D = +56°$ (chloroform). UV: $\epsilon_{240} = 16,800$ (methanol).

EXAMPLE 4

(A) 4.85 g of 6β,7β;15β,16β-dimethylene-3-oxo-17α-pregn-4-ene-21,17-carbolactone is stirred in 72.8 ml of 2-propanol with 15.5 ml of a 1N potassium hydroxide solution in methanol for 30 minutes at 70° C. The ice-cooled reaction solution is stirred into 700 ml of ice-cooled diethyl ether. The thus-obtained precipitate is suctioned off, washed with diethyl ether, and dried, yielding 4.5 g of 17-hydroxy-6β,7β;15β,16β-dimethylene-3-oxo-17α-pregn-4-ene-21-carboxylic acid potassium salt, mp 189° C.

(B) 1.0 g of 17-hydroxy-6β,7β;15β,16β-dimethylene-3-oxo-17α-pregn-4-ene-21-carboxylic acid potassium salt is stirred in 9 ml of hexamethylphosphoric triamide with 1 ml of methyl iodide for 1 hour at room temperature. The reaction solution is diluted with diethyl ether, washed with water, dried, and evaporated. The residue is chromatographed on silica gel, thus obtaining 900 mg of 17-hydroxy-6β,7β;15β,16β-dimethylene-3-oxo-17α-pregn-4-ene-21-carboxylic acid methyl ester as an oil. UV: $\epsilon_{267} = 18,400$ (methanol). $[\alpha]_D = -195°$ (chloroform).

EXAMPLE 5

1.0 g of 17-hydroxy-6β,7β;15β,16β-dimethylene-3-oxo-17α-pregn-4-ene-21-carboxylic acid potassium salt is reacted, as described in Example 4(B), in 9 ml of hexamethylphosphoric triamide with 1 ml of ethyl bromide, and worked up. Chromatography on silica gel yields 890 mg of 17-hydroxy-6β,7β;15β,16β-dimethylene-3-oxo-17α-pregn-4-ene-21-carboxylic acid ethyl ester as an oil.

UV: $\epsilon_{268} = 18,200$ (methanol). $[\alpha]_D = -193°$ (chloroform).

EXAMPLE 6

1.0 g of 17-hydroxy-6β,7β;15β,16β-dimethylene-3-oxo-17α-pregn-4-ene-21-carboxylic acid potassium salt is reacted, as disclosed in Example 4(B), in 9 ml of hexamethylphosphoric triamide with 1 ml of propyl bromide and worked up. After chromatography on silica gel, 990 ml of 17-hydroxy-6β,7β;15β,16β-dimethylene-3-oxo-17α-pregn-4-ene-21-carboxylic acid propyl ester is obtained as an oil.

UV: $\epsilon_{267} = 18,500$ (methanol). $[\alpha]_D = -188°$ (chloroform).

EXAMPLE 7

1.0 g of 17-hydroxy-6β,7β;15β,16β-dimethylene-3-oxo-17α-pregn-4-ene-21-carboxylic acid potassium salt is reacted as described in Example 4(B) in 9 ml of hexamethylphosphoric triamide with 1 ml of pentyl bromide, and worked up. Chromatography on silica gel yields 960 mg of 17-hydroxy-6β,7β;15β,16β-dimethylene-3-oxo-17α-pregn-4-ene-21-carboxylic acid pentyl ester as an oil.

UV: $\epsilon_{267} = 18,100$ (methanol). $[\alpha]_D = -176°$ (chloroform).

EXAMPLE 8

(A) 4.0 g of 6β,7β;15β,16β-dimethylene-3-oxo-17α-pregna-1,4-diene-21,17-carbolactone is stirred in 60 ml of 2-propanol with 12.7 ml of a 1N potassium hydroxide solution in methanol for 30 minutes at 85° C. The reaction mixture is worked up as described in Example 4(A), thus isolating 3.5 g of 17-hydroxy-6β,7β;15β,16β-dimethylene-3-oxo-17α-pregna-1,4-diene-21-carboxylic acid potassium salt, mp 166°–172° C.

(B) 1.0 g of 17-hydroxy-6β,7β;15β16β-dimethylene-3-oxo-17α-pregna-1,4-diene-21-carboxylic acid potassium salt is reacted as disclosed in Example 4(B) in 9 ml of hexamethylphosphoric triamide with 1 ml of methyl iodide and worked up. Chromatography on silica gel yields 860 mg of 17-hydroxy-6β,7β;15β,16β-dimethylene-3-oxo-17α-pregna-1,4-diene-21-carboxylic acid methyl ester as an oil.

UV: $\epsilon_{245}=11,200$; $\epsilon_{286}=9,800$ (methanol). $[\alpha]_D = -186°$ (chloroform).

EXAMPLE 9

810 mg of 17-hydroxy-6β,7β;15β16β-dimethylene-3-oxo-17α-pregna-1,4-diene-21-carboxylic acid potassium salt is reacted as described in Example 4(B) in 81 ml of hexamethylphosphoric triamide with 0.81 ml of propyl bromide, and worked up. After trituration with diisopropyl ether, 710 mg of 17-hydroxy-6β,7β;15β,16β-dimethylene-3-oxo-17α-pregna-1,4-diene-21-carboxylic acid propyl ester is produced, mp 136.5° C. UV: $\epsilon_{245}=11,500$; $\epsilon_{286}=10,000$ (methanol).

EXAMPLE 10

As described in Example 4(B), 1.0 g of 17-hydroxy-6β,7β;15β,16β-dimethylene-3-oxo-17α-pregna-1,4-diene-21-carboxylic acid potassium salt is reacted in 9 ml of hexamethylphosphoric triamide with 1 ml of butyl bromide and worked up. After chromatography on silica gel, 940 mg of 17-hydroxy-6β,7β;15β,16β-dimethylene-3-oxo-17α-pregna-1,4-diene-21-carboxylic acid butyl ester is obtained as an oil.

UV: $\epsilon_{244}=11,000$; $\epsilon_{286}=9,700$ (methanol). $[\alpha]_D = -178°$ (chloroform).

EXAMPLE 11

(A) 1.8 g of 6β,7β-methylene-3-oxo-17α-pregn-4-ene-21,17-carbolactone is stirred in 18 ml of 2-propanol with 5 ml of a 1N potassium hydroxide solution in methanol for 30 minutes at 70° C. The mixture is worked up as disclosed in Example 4(A), thus obtaining 1.5 g of 17-hydroxy-6β,7β-methylene-3-oxo-17α-pregn-4-ene-21-carboxylic acid potassium salt, mp 264° C.

(B) 500 mg of 17-hydroxy-6β,7β-methylene-3-oxo-17α-pregn-4-ene-21-carboxylic acid potassium salt is stirred in 10 ml of dimethyl sulfoxide with 0.5 ml of methyl iodide for one hour at room temperature and worked up as described in Example 4(B). Chromatography on silica gel yields 450 mg of 17-hydroxy-6β,7β-methylene-3-oxo-17α-pregn-4-ene-21-carboxylic acid methyl ester as an oil.

UV: $\epsilon_{265}=18,500$ (methanol). $[\alpha]_D = -195°$ (chloroform).

EXAMPLE 12

As described in Example 4(B), 500 mg of 17-hydroxy-6β,7β-methylene-3-oxo-17α-pregn-4-ene-21-carboxylic acid potassium salt is reacted in 10 ml of dimethyl sulfoxide with 0.5 ml of propyl bromide and worked up. Chromatography on silica gel yields 430 mg of 17-hydroxy-6β,7β-methylene-3-oxo-17α-pregn-4-ene-21-carboxylic acid propyl ester as an oil.

UV: $\epsilon_{266}=18,700$ (methanol). $[\alpha]_D = -182°$ (chloroform).

EXAMPLE 13

(A) 1.5 g of 6α,7α-methylene-3-oxo-17α-pregn-4-ene-21,17-carbolactone is stirred in 15 ml of 2-propanol with 4.15 ml of a 1N potassium hydroxide solution in methanol for 30 minutes at 70° C. The mixture is then worked up as set forth in Example 4(A), thus obtaining 1.34 g of 17-hydroxy-6α,7α-methylene-3-oxo-17α-pregn-4-ene-21-carboxylic acid potassium salt, mp 249°–254° C. (under decomposition).

(B) As described in Example 4(B), 500 mg of 17-hydroxy-6α,7α-methylene-3-oxo-17α-pregn-4-ene-21-carboxylic acid potassium salt is reacted in 10 ml of dimethyl sulfoxide with 0.5 ml of propyl bromide and worked up. After chromatography on silica gel, 450 mg of 17-hydroxy-6α,7α-methylene-3-oxo-17α-pregn-4-ene-21-carboxylic acid propyl ester is obtained as an oil. UV: $\epsilon_{259}=17,000$ (methanol). $[\alpha]_D = +90°$ (chloroform).

EXAMPLE 14

(A) 1.5 g of 6-methyl-3-oxo-17α-pregna-4,6-diene-21,17-carbolactone is stirred in 15 ml of 2-propanol with 4.15 ml of a 1N potassium hydroxide solution in methanol for 30 minutes at 70° C. The mixture is worked up as set forth in Example 4(A), thus obtaining 1.48 g of 17-hydroxy-6-methyl-3-oxo-17α-pregna-4,6-diene-21-carboxylic acid potassium salt, mp 242°–246° C. (under decomposition).

(B) 500 mg of 17-hydroxy-6-methyl-3-oxo-17α-pregna-4,6-diene-21-carboxylic acid potassium salt is reacted as described in Example 4(B) in 10 ml of dimethyl sulfoxide with 0.5 ml of methyl iodide and worked up, thus producing 480 mg of 17-hydroxy-6-methyl-3-oxo-17α-pregna-4,6-diene-21-carboxylic acid methyl ester as an oil.

UV: $\epsilon_{289}=22,800$ (methanol). $[\alpha]_D = -1.3°$ (chloroform).

EXAMPLE 15

As described in Example 4(B), 500 mg of 17-hydroxy-6-methyl-3-oxo-17α-pregna-4,6-diene-21-carboxylic acid potassium salt is reacted in 10 ml of dimethyl sulfoxide with 0.5 ml of propyl bromide and worked up. Chromatography on silica gel yields 430 mg of 17-hydroxy-6-methyl-3-oxo-17α-pregna-4,6-diene-21-carboxylic acid propyl ester, mp 145° C. UV: $\epsilon_{288}=23,100$ (methanol). $[\alpha]_D = -2.3°$ (chloroform).

EXAMPLE 16

(A) A solution of 3.0 g of 15β,16β-methylene-3-oxo-17α-pregn-4-ene-21,17-carbolactone in 45 ml of 2-propanol is combined with 9 ml of a 1N potassium hydroxide solution in methanol, and the mixture is refluxed for 30 minutes. After cooling, the reaction mixture is introduced into 450 ml of ice-cold diethyl ether; the precipitate is filtered off and washed with diethyl ether. Yield: 3.1 g of 17-hydroxy-15β,16β-methylene-3-oxo-17α-pregn-4-ene-21-carboxylic acid potassium salt.

(B) A solution of 1.0 g of 17-hydroxy-15β,16β-methylene-3-oxo-17α-pregn-4-ene-21-carboxylic acid potassium salt in 10 ml of dimethyl sulfoxide is combined with 1 ml of methyl iodide and the mixture is agitated for 2 hours at room temperature. After stirring into water, the mixture is extracted with dichloromethane, washed with sodium bicarbonate solution and water, dried over sodium sulfate, and concentrated under vacuum. The resultant crude product is purified by column chromatography on silica gel with hexane-ethyl acetate, thus obtaining 480 mg of 17-hydroxy-15β,16β-methylene-3-oxo-17α-pregn-4-ene-21-carboxylic acid methyl ester.

EXAMPLE 17

Under the conditions described in Example 16(B), 900 mg of 17-hydroxy-15β,16β-methylene-3-oxo-17α-pregn-4-ene-21-carboxylic acid potassium salt and 1 ml of ethyl bromide as the starting materials yield 440 mg of 17-hydroxy-15β,16β-methylene-3-oxo-17α-pregn-4-ene-21-carboxylic acid ethyl ester. $[\alpha]_D = +41°$ (chloroform). UV: $\epsilon_{238} = 14,800$ (methanol).

EXAMPLE 18

Under the conditions disclosed in Example 16(B), 1.0 g of 17-hydroxy-15β,16β-methylene-3-oxo-17α-pregn-4-ene-21-carboxylic acid potassium salt and 1 ml of propyl bromide as the starting materials yield 400 mg of 17-hydroxy-15β,16β-methylene-3-oxo-17α-pregn-4-ene-21-carboxylic acid propyl ester. $[\alpha]_D = +41°$ (chloroform). UV: $\epsilon_{239} = 15,000$ (methanol).

EXAMPLE 19

(A) Under the conditions described in Example 16(A), 1.0 g of 7α-methoxycarbonyl-15β,16β-methylene-3-oxo-17α-pregn-4-ene-21,17-carbolactone yields 980 mg of 17-hydroxy-7α-methoxycarbonyl-15β,16β-methylene-3-oxo-17α-pregn-4-ene-21-carboxylic acid potassium salt.

(B) Under the conditions set forth in Example 16(B), 980 mg of 17-hydroxy-7α-methoxycarbonyl-15β,16β-methylene-3-oxo-17α-pregn-4-ene-21-carboxylic acid potassium salt and 1 ml of ethyl bromide as the starting materials yield 395 mg of 17-hydroxy-7α-methoxycarbonyl-15β,16β-methylene-3-oxo-17α-pregn-4-ene-21-carboxylic acid ethyl ester.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 17α-pregn-4-ene-3-oxo-21-carboxylic acid ester of the formula

[chemical structure]

wherein
$C_1 = C_2$ is a CC single or C=C double bond;
—A—B— is

[chemical structures]

—C—D— is

[chemical structures]

and
R is $C_{1-6}$-alkyl or $C_{2-6}$-alkenyl.

2. 17-hydroxy-3-oxo-17α-pregn-4-ene-6β,7β; 15β,16β-dimethylene-21-carboxylic acid methyl ester, a compound of claim 1.

3. 17-hydroxy-3-oxo-17α-pregn-4-ene-6β,7β; 15β,16β-dimethylene-21-carboxylic acid ethyl ester, a compound of claim 1.

4. 17-hydroxy-3-oxo-17α-pregn-4-ene-6β,7β; 15β,16β-dimethylene-21-carboxylic acid propyl ester, a compound of claim 1.

5. 17-hydroxy-3-oxo-17α-pregn-4-ene-6β,7β; 15β,16β-dimethylene-21-carboxylic acid pentyl ester, a compound of claim 1.

6. A pharmaceutical composition containing an amount of a compound of claim 1 effective as an antialdosterone agent and a pharmacologically acceptable carrier.

7. A pharmaceutical composition of claim 6 containing two of said compounds.

8. A pharmaceutical composition of claim 1 wherein the amount of said compound is 10–100 mg.

9. A pharmaceutical composition of claim 6 adapted for oral administration.

10. A method of achieving an antialdosterone effective in a patient in need of such treatment comprising administering an amount of a compound of the following formula effective as an antialdesterone agent

[chemical structure]

wherein
$C_1 = C_2$ is a CC single or C=C double bond;
—A'B— is

[chemical structures]

—C—D— is

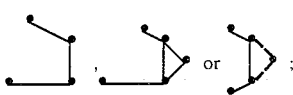

and

R is $C_{1-6}$-alkyl or $C_{2-6}$-alkenyl.

11. A method of achieving a diuretic effect in a patient in need of such treatment comprising administering to the patient a diuretically effective amount of a compound of the formula

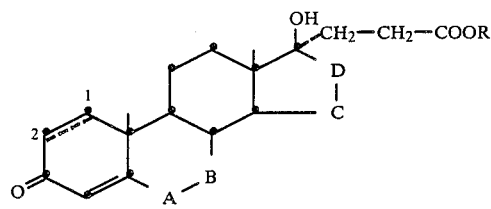

wherein
$C_1$=====$C_2$ is a CC single or C═C double bond;
—A—B— is

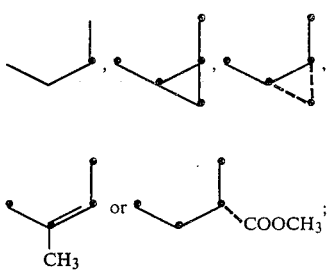

—C—D— is

and
R is $C_{1-6}$-alkyl or $C_{2-6}$-alkenyl.

12. A 17α-pregn-4-ene-3-oxo-21-carboxylic acid ester of the formula

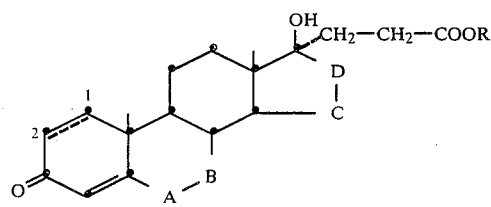

wherein
$C_1$=====$C_2$ is a CC single or C═C double bond;
—A—B— is

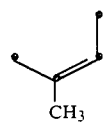

—C—D— is

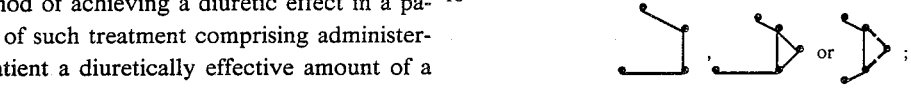

and
R is $C_{1-6}$-alkyl or $C_{2-6}$-alkenyl.

13. A 17α-pregn-4-ene-3-oxo-21-carboxylic acid ester of the formula

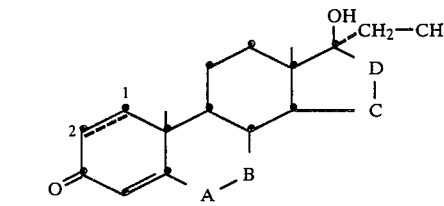

wherein
$C_1$=====$C_2$ is a CC single or C═C double bond;
—A—B— is

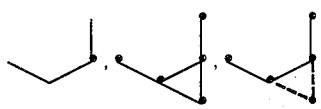

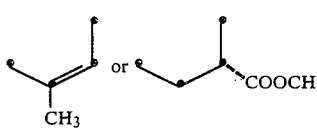

—C—D— is

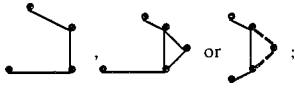

and
R is $C_{2-6}$-alkenyl.

14. A 17α-pregn-4-ene-3-oxo-21-carboxylic acid ester of the formula

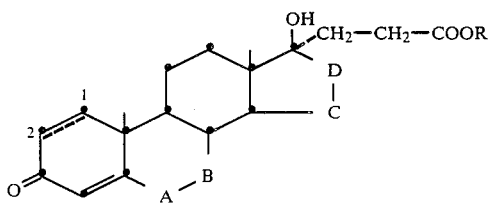

wherein
$C_1$=====$C_2$ is a CC single bond;
—A—B— is

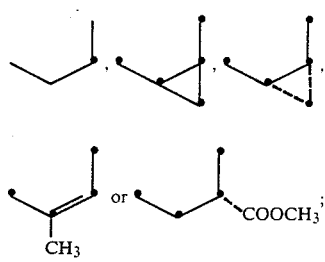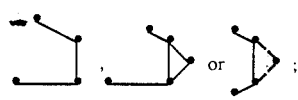

—C—D— is

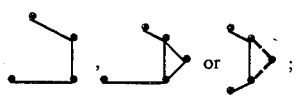

and
R is $C_{1-6}$-alkyl or $C_{2-6}$-alkenyl.

15. A 17α-pregn-4-ene-3-oxo-21-carboxylic acid ester of the formula

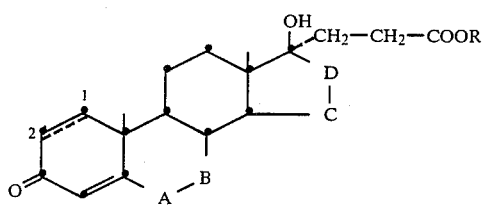

wherein
$C_1\text{=====}C_2$ is a CC single bond or a C=C double bond;
—A—B— is

—C—D— is

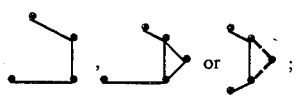

and
R is $C_{1-6}$-alkyl or $C_{2-6}$-alkenyl.

16. A 17α-pregn-4-ene-3-oxo-21-carboxylic acid ester of the formula

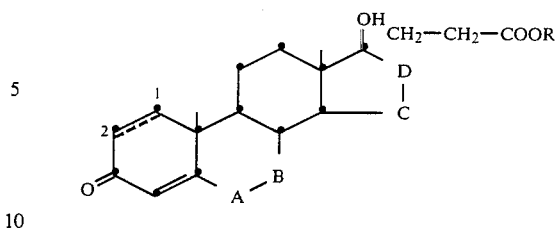

wherein
$C_1\text{=====}C_2$ is a CC single or C=C double bond;
—A—B— is

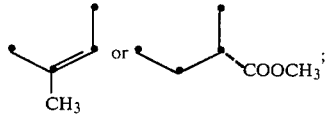

—C—D— is

and
R is $C_{1-6}$-alkyl or $C_{2-6}$-alkenyl.

17. A pharmaceutical composition containing an amount of a compound of claim 12 effective as an antialdosterone agent and a pharmacologically acceptable carrier.

18. A pharmaceutical composition containing an amount of a compound of claim 13 effective as an antialdosterone agent and a pharmacologically acceptable carrier.

19. A pharmaceutical composition containing an amount of a compound of claim 14 effective as an antialdosterone agent and a pharmacologically acceptable carrier.

20. A pharmaceutical composition containing an amount of a compound of claim 15 effective as an antialdosterone agent and a pharmacologically acceptable carrier.

21. A pharmaceutical composition containing an amount of a compound of claim 16 effective as an antialdosterone agent and a pharmacologically acceptable carrier.

* * * * *